United States Patent [19]

Trivett et al.

[11] Patent Number: 4,923,612

[45] Date of Patent: May 8, 1990

[54] FLUID RECOVERY AND TRANSFER SYSTEM

[76] Inventors: Gordon S. Trivett, P.O. Box 213114, Tantallon, Nova Scotia B0J 3J0; John L. Leahey, 17 Wedgewood Ave., Halifax N.S., B3M 2B2, both of Canada

[21] Appl. No.: 224,297

[22] Filed: Jul. 26, 1988

[51] Int. Cl.⁵ .............................................. B01D 13/00
[52] U.S. Cl. .................................. 210/646; 210/136; 210/351; 210/416.1
[58] Field of Search .................... 210/321.67, 500.24, 210/136, 416.1, 646; 417/393, 395

[56] References Cited

U.S. PATENT DOCUMENTS 3,570,672  3/1971  Bach ................................ 210/139 X
3,673,612  7/1972  Merrill et al. ............... 210/500.24 X
4,624,628  11/1986  Marchant ........................... 417/393

Primary Examiner—Frank Spear
Attorney, Agent, or Firm—Banner, Birch, McKie and Beckett

[57] ABSTRACT

A fluid recovery and transfer system utilizes hydraulic pressure on a plurality of collapsible containers to effect the alternate intake and output of a fluid from the collapsible containers. The hydraulic pressure is generated through the pumping of a plump fluid to and from a plurality of rigid containers within which the collapsible containers are disposed. The pumping of the pump fluid alternately creates positive and negative pressures within the collapsible containers to draw in the body fluid and to subsequently eject the body fluid. The fluids recovered in such a manner may either be stored, processed, or retransfused back to the body.

23 Claims, 4 Drawing Sheets

FIG. 4
FIG. 4A
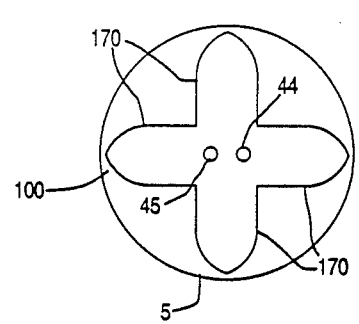
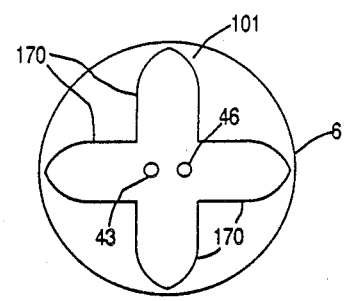

FLUID RECOVERY AND TRANSFER SYSTEM

The present invention generally relates to a fluid suction transfer and delivery system and specifically relates to a medical fluid recovery and transfer system having a hydraulic pump which alternately uses positive and negative pressure to recover body fluids and either store, process, or retransfuse the recovered fluids.

BACKGROUND OF THE INVENTION

In many medical procedures, body fluids are recovered from a patient in order to be stored, processed and treated, or retransfused back to the body. Perhaps the most well known of procedures of this type involve the recovery of blood from a patient during surgical operations. The patient is coupled to a heart/lung machine which recovers blood from the patient by means of pumps associated with the machine and subsequently retransfuses the blood back to the patient. However, pumping machines of this type are generally expensive and subject the blood being collected to significant trauma during the pumping cycle. This is particularly critical when blood is the recovered fluid since the trauma generated in prior art systems which use either roller pumps or diaphragm pumps generate micro emboli which can affect the retransfused blood an cause harmful reactions in the patient. The trauma may also cause direct physical damage to a medical fluid, particularly blood.

At present, there is increased concern about the use of donor blood during surgical procedures because of the potential of contracting various diseases. Although in many instances donor blood is a necessity, the retransfusing of one's own blood offers a number of advantages. There is no need to match the donor with the patient, a problem which may arise in the case of an uncommon blood type. Perhaps more importantly there is a reduced risk of introducing potentially harmful substances into the blood. Autotransfused blood is also fresh and there is no cost associated with its storage and reprocessing as in the case of donor blood.

The recovery of body fluids is not limited to that of blood during surgical procedures. Other procedures include the suction irrigation of joints for infection, suction irrigation for dialysis (either peritoneal or extra corporeal), gastrointenstinal or urological fluid exchange, and suction recovery of cerebral spinal fluid (CSF) in hydrocephalus.

SUMMARY OF THE INVENTION

It is an object of the present invention to provide a fluid recovery and transfer system which is simple to operate and maintain.

It is a further object of the present invention to provide a fluid recovery and transfer system which reduces mechanical damage to the recovered fluid during system operation.

It is still a further object of the present invention to provide a fluid recovery and transfer system which is compatible with the sterility requirements and standard packaging of medical fluid products.

It is still a further object of the present invention to provide a fluid recovery and transfer system in which the recovery of body fluids is effected by the application of hydraulic pressure to a collapsible container.

It is still a further object of the present invention to provide in an alternate embodiment a fluid recovery and transfer system having a semi-permeable collapsible container which can be operated as a dialysis unit.

According to the present invention a fluid recovery and transfer system includes a plurality of rigid containers. A collapsible container is disposed within each of the rigid containers. Each of the collapsible containers is coupled to a common intake and a common output for a fluid. A pump means pumps a pump fluid to and from each of the rigid containers to hydraulically effect the alternate intake and output of the fluid from each of the collapsible containers.

BRIEF DESCRIPTION OF THE DRAWINGS

A more complete appreciation of the invention and many of the attendant advantages thereof will be readily obtained as the invention becomes better understood by reference to the following detailed description when considered in connection with the accompanying drawings wherein:

FIG. 4 is an overhead view of the rigid enclosures of FIG. 3 showing the vertical pleats of collapsible containers suitable for dialysis.

DETAILED DESCRIPTION OF PREFERRED EMBODIMENT

Figure 1:
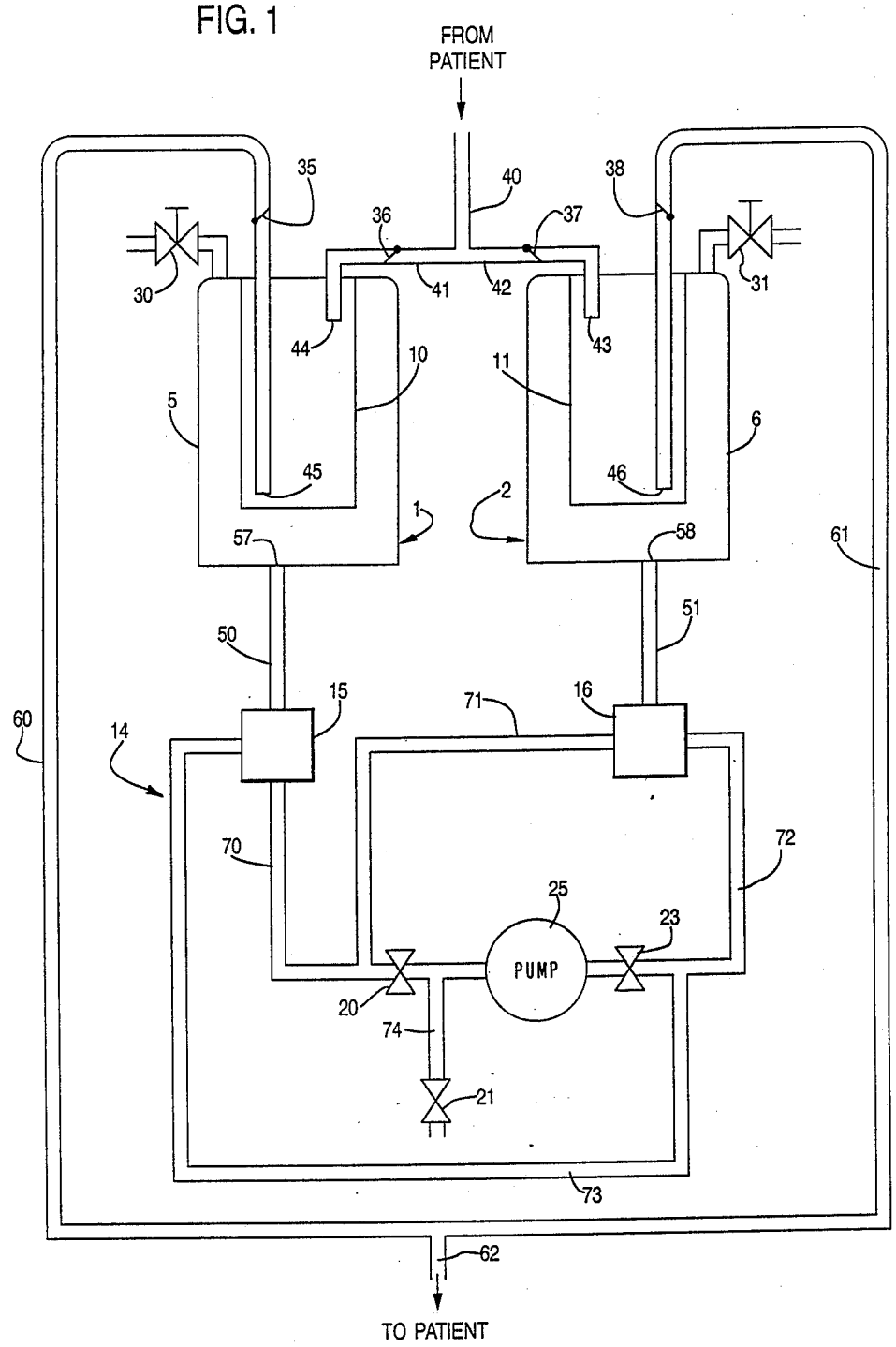
FIG. 1 is a schematic representation of a fluid recovery and transfer system according to the present invention.

The apparatus shown in FIG. 1 includes two chambers, generally indicated as 1 and 2. Chamber 1 includes a jacket or rigid container 5 and a collapsible container 10. Chamber 2 is similarly configured to include a jacket or rigid container 6 and a collapsible container 11. The collapsible containers may be standard intravenous surgical bags commonly used in hospitals (Abott or equivalent). Alternatively, the collapsible container may be constructed of a semipermeable membrane for dialysis applications. To ensure sterile conditions the collapsible containers are replaced after each patient use. The collapsible containers are preferably spaced from the inside walls of the rigid containers.

Vents 30 and 31 are coupled to jackets 5 and 6 respectively and serve to release any trapped gas or air which may be generated during the pumping and/or filling operations. Vents 30 and 31 also serve to provide a pressure bypass in the case of overpressurization of the pumping system, to provide a vacuum lock during the suction cycles of containers 10 and 11 and to facilitate drainage upon the completion of use of the device.

Collapsible containers 10 and 11 are respectively coupled to intake and output circuits. Tubing 60 couples container 10 to output 62 and tubing 61 couples container 11 to output 62. Containers 10 and 11 are coupled to common intake 40 through tubings 41 and 42, respectively. The preferred particularly for blood processing applications is heprin impregnated polyethylene tubing typically available in a hospital transplantation environment. The tubing size can be ⅜ or ¼ inch nominal tubing. Check valves 35, 36, 37, and 38, in tubing 60, 41, 42 and 61 respectively are responsive to pressure changes during the pumping operation and control the fluid flow in the respective tubings. Valves 35, 36, 37, and 38 are low pressure, low differential pressure activation, and low abrasion type vales. Valves which may be used include cardiac-type valves typically available in hospitals or equivalent valves.

The pumping circuit of the present invention is generally designated as 14. The pump circuit serves to transfer a pump fluid between jackets 5 and 6. The pump fluid used in the pumping circuit should be a body compatible fluid, e.g. normal saline, Ringer's lactate, glucose and water, etc. In the preferred embodiment, the pumping circuit is sized such that approximately 5 to 7 liters of the pump fluid is charged to the pump system prior to patient connection. Solenoids 15 and 16 control the direction of fluid flow between jackets 5 and 6. An arrangement of tubing, described in more detail below, permits the flow of the pump fluid between the jackets. This pumping circuit tubing can be standard polyethylene tubing or stainless steel pipe. The tubing size is typically ½ inch nominal diameter. Fill switches 20 and 21 enable the pumping circuit to be charged with the body compatible pump fluid from a storage reservoir and contain the pump fluid within the closed pumping circuit. Valve 23 is used to control the flow rate form the outlet side of pmp 25. Pump 25 can be any positive displacement pump; the design of pump 25 not being a critical feature of the present invention. Preferably, those portions of the pump which will be in contact with the pump fluid are made of or coated with a corrosion resistant material such as stainless steel, teflon or the like.

Operation of the above-described fluid recovery and transfer system will now be described with reference to FIG. 1. Intake 40 is coupled to the patient in a manner appropriate to the recovery of the fluid of interest. A citrate injector may be in parallel with the input tubing 40 so that for a given volume of collected blood the correct amount of citrate or other anti-coagulant may be infused to prevent the blood from clotting. If the recovered fluid is to be returned to the patient, outlet 62 also is appropriately coupled to the patient. Alternatively, outlet 62 may be externally coupled so as to store the recovered fluid for future use or to dispose of the recovered fluid.

Procedures to which this invention may be directed include but are not limited to, the suction irrigation of joints for infection, suction irrigation for dialysis (either peritoneal or extra corporeal), suction recovery for cerebral spinal fluid (CSF) in hydraocephalus, gastrointestinal or urological fluid exchange, and blood recovery and processing during various medical procedures. The system can be used for blood collection during operations for retransfusion during the same procedure or at a later time. The system may also be used as a complete extracorporeal system while the patient is on heart bypass or awaiting heart replacement. The system has particular utility as a blood dialysis unit.

Hydraulic pressure of pump fluid generated by pump 25 in pumping circuit 14 acts on a collapsible bag containing the medical fluid of interest such as blood, blood products, and irrigation fluids for surgery and other procedures. Pump fluid gauge pressure in the range of about 50 to 150 mm Hg are suitable during operation of the present invention. With the patient hooked up to the system, fluid recovery may be effected by alternately producing negative and positive pressures in containers 10 and 11. These positive and negative pressures are created by the operation of pump 25 during the pumping cycle to be described below.

Immediately prior to operation, one of the collapsible containers, eg. 10, is empty and the other, eg. 11 is filled with approximately one liter of body compatible fluid or blood. During the first half of the cycle, pump fluid from jacket 5 is pumped to jacket 6. Pump fluid from jacket 5 enters tubing 50 through opening 57 and is pumped from tubing 50 through respective tubings 70, 72 and 51 before entering jacket 6 through opening 58. The pumping of the pump fluid from jacket 5 causes a negative pressure within container 10 and draws body fluid from the patient, past check valve 36 and into container 10. This intake of body fluid from the patient into container 10 continues as the pump fluid is being pumped from jacket 5. As pump fluid is pumped into jacket 6, body fluid stored in container 11 initially or during a previous pumping cycle is forced into outflow tubing 61 through opening 46 and past check valve 38. Check valve 37 prevents any body fluid from container 11 from entering the intake system through tubing 42. The body fluid from container 11 passes through tubing 61 to output 62. Openings 45 in container 10 and 46 in container 11 should preferably extend to a position proximate to the bottom of the corresponding container and are appropriately configured to prevent any obstruction to the egress of the body fluid from the containers during operation.

Once container 10 is filled with body fluid and container 11 has been emptied, solenoids 15 and 16 reverse the flow direction of pump fluid so that it is now pumped form jacket 6 to jacket 5. Pump fluid from jacket 6 enters tubing 51 via opening 58 and is pumped from tubing 51 through respective tubings 71, 72 and 50 from where it enters jacket 5 through opening 57. The pumping of pump fluid from jacket 6 causes a negative pressure within container 11 and draws body fluid from the patient, past check valve 37 and into container 11. The intake of body fluid from the patient into container 11 continues as the pump fluid is being pumped from jacket 6. As pump fluid is pumped into jacket 5, body fluid stored in container 10 during the first half of the pumping cycle is forced into outflow tubing 60 via opening 45 and past check valve 35. Check valve 36 prevents any body fluid in container 10 from entering the intake system via tubing 41. The body fluid from container 10 passes through tubing 60 to output 62. Check valve 38 prevents body fluid from re-entering container 11 through tubing 61 while container 10 is being emptied and container 11 is being filled. Similarly, during the emptying of container container 11 through tubing 61, check valve 35 prevents body fluid from re-entering container 10 through tubing 60.

The body fluid recovered at output 62 may be treated or processed in a number of ways, particularly if it is to be returned to the patient. It may be passed through a cyclone filter which allows any air collected with the fluid to escape; or it may be oxygenated as now accomplished in known heart and lung machines. Particulate matter may also be filtered. The blood may be rewarmed with a conventional blood rewarming unit if it is to be immediately retransfused to the patient. Alternatively, the collected fluid may be stored for future use.

The presently preferred embodiments of the invention utilize a unidirectional pump. Otherwise the lag time for flow direction change would be inordinately long and inhibit the proper functioning of the medical fluid recovery system. While unidirectional pumps are used in the presently preferred embodiments, the invention should be broadly construed to embrace any pump mechanism which can effect rapid change in flow direction.

The fluid recovery and transfer system described above offers a major advantage over the current technology in preserving the quality of the blood by avoiding mechanical damage through the pumping action. During operation of the system according to the present invention, uniformly distributed pressures inherently are exerted across the collapsible container. This prevents high impact loads or concentrated pressures from acting on the body fluid during forward propulsion. This minimizes trauma. Trauma or mechanical damage generated in prior art roller pump or diaphragm pumps generate micro emboli which can be adversely affect the quality of the collected blood.

In addition, uniformly distributed pressures reduce direction physical damages to the medical fluid, notably the blood cells. The present invention also is compatible with sterility requirements and the conventional packaging of medical fluid products in flexible plastic bags. The system is simple to operate and maintain and avoids the use of a large number of moving parts. The system is easily sterilized prior to use by flowing a suitable purgative such as ethylene oxide or, in certain cases, stream through the equipment.

The system operated as described above eliminates the possibility of an air embolism in the case of a catastrophic failure of the collapsible container. If such a catastrophic failure were to occur, the pump would continue to pump body compatable fluids to the patient while corrective procedures were being effected.

The present invention offers a further advantage over the prior art in that pulsatile flow may be provided through simple modulation of the output of the pump with respect to the pump fluid. The valving mechanism 232 for providing the pulsatile flow is variable so as to permit the system to be adjusted to the requirements of a given patient or other situations. Other adjustable parameters include body fluid flow rate, the body fluid temperature, and the pressure on the body fluid.

Figure 2:
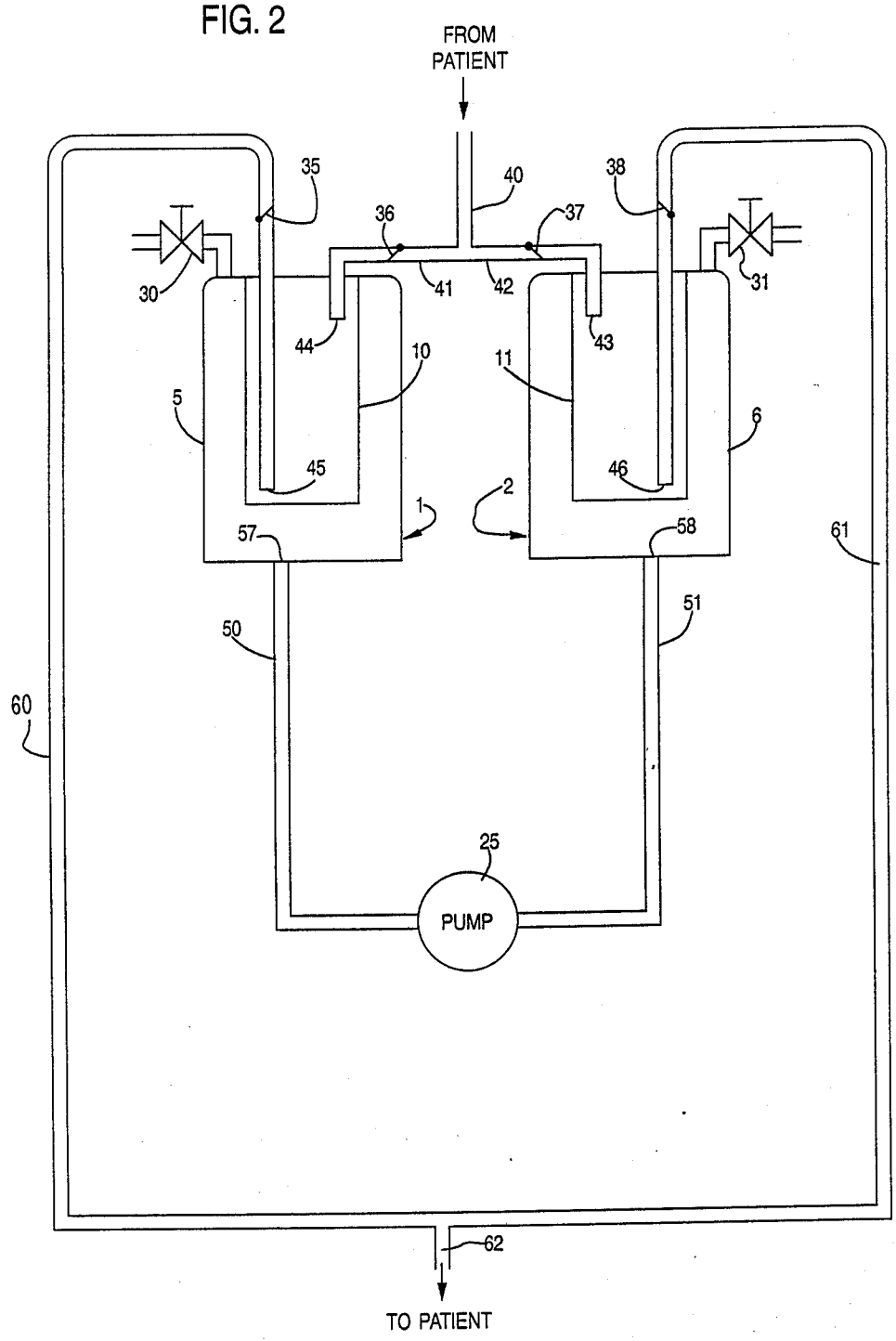
FIG. 2 is a schematic representation of a fluid recovery and transfer system according to another embodiment of the present invention.

The present invention may be modified in a number of ways. Although the above-described system discloses two chambers to permit continuous operation of the pump system, other desirable configurations with a plurality of chambers exist which permit body fluid selection and provide for redundancy in the event of a failure in the system. In addition, although the above-described embodiment includes a unidirectional pump for pumping the pump fluid between the jackets, other pumps may be used as indicated schematically in FIG. 2 wherein the same reference numerals are used to indicate those system components which are common with FIG. 1.

Figure 3:
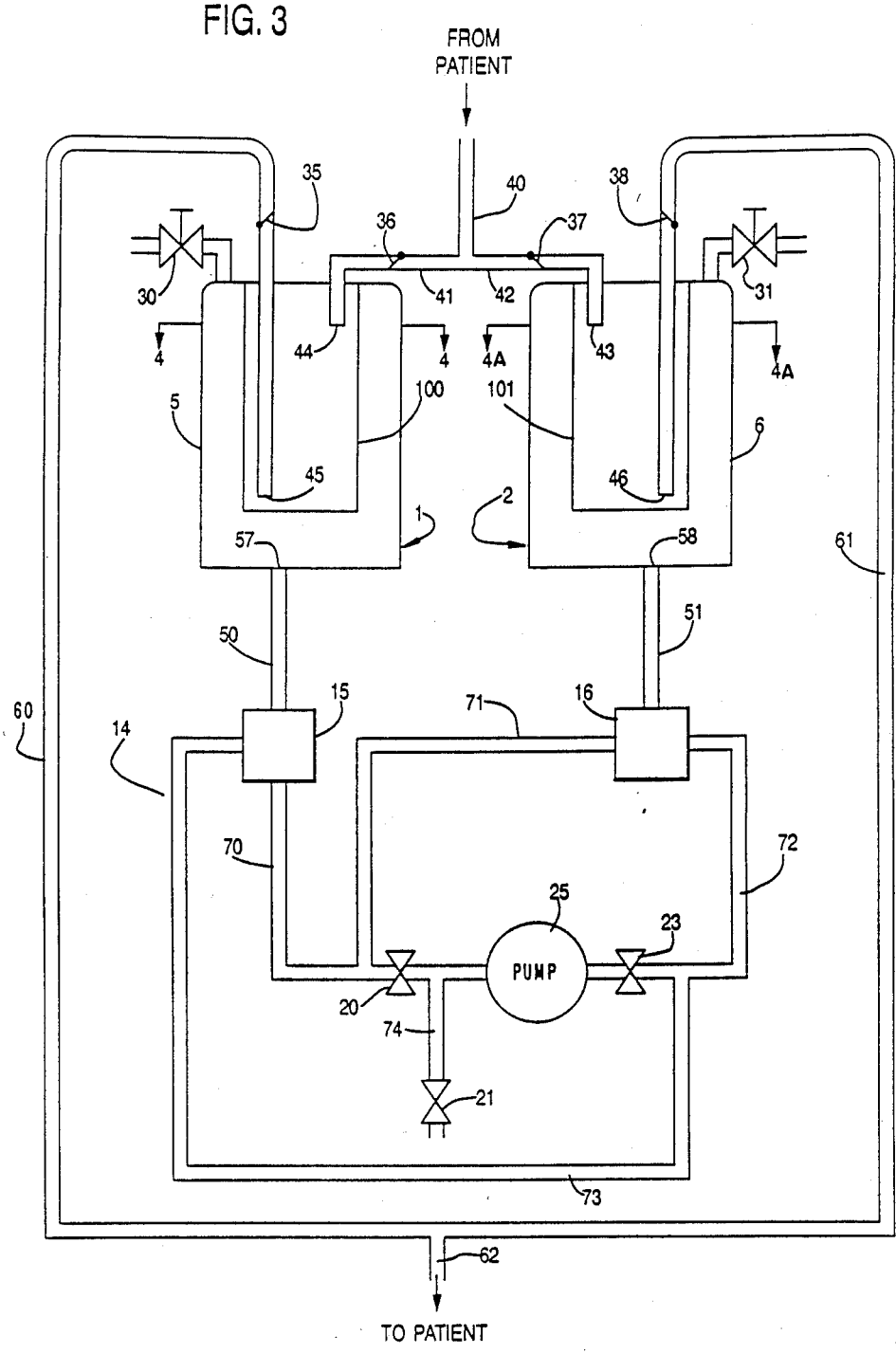
FIG. 3 is a schematic representation of a fluid recovery and transfer system according to a further embodiment of the present invention.

The transfer and delivery system of the present invention has particular utility as a blood dialyzer. When the above-described system is used for blood dialysis, collapsible semi-permeable membranes 100 and 101 which preferably are of a corrugated configuration to provide a maximum amount of cross sectional area available for mass transfer replace containers 10 and 11 as shown in FIG. 3 and the system operation remains the same. The semi-permeable membrane should resist passage of substances of molecular weight greater than about 10,000. Suitable membrane materials include cuprammonium cellulose, polyacrylonitrite (PAN), polymethylmethacrylate (PMMA) and polycarbonate, with an appropriate pore size, e.g. about 4 microns, for dialysis applications. In this embodiment, the pump fluid is a dialysate fluid having a composition well known to those skilled in the dialysate art. The composition of the dialysate fluid is such that during operation of the system, body waste products are transferred across the membrane from the body fluid (e.g. blood) into the dialysate pump fluid. As recognized by those skilled in this art, the rate at which body waste products are removed from the body fluid can be controlled by the concentration gradient established between the body fluid and the pump fluid and also is influenced by the pressure gradient developed during operation of the pumping circuit. By establishing appropriate concentration gradients, bioaffecting or bioactive materials also can be transferred across the membrane from the pump fluid into the body fluid.

One embodiment of the semi-permeable dialysis bag features four vertical pleats 170 as shown in the overhead view of FIG. 4 of the rigid enclosures. The number of pleats may be varied and the invention should not be understood as limited in this respect. One of ordinary skill may empirically determine the most efficient number of pleats in terms of presenting increased surface area as weighed against the cost of manufacture and the complexities of operation. It is also possible to configure the collapsible dialysis bag with horizontal oriented pleating (not shown).

The invention also may be applied to specialized treatments requiring the exposure of body fluids, particularly blood, to a drug or other substance, such as an enzyme (e.g. urease), or a combination thereof, which could be supported or bound on the interior surface or contained in the pump fluid of the collapsible container. This would be of prime importance where it would be desirable that the drug or other substance actually be introduced into the body of the patient. Detoxification of blood or other body fluids are examples of this application.

While the foregoing description is directed to a presently preferred embodiment, it will be obvious to one of ordinary skill that various modifications may be made without departing from the true spirit or scope of the invention, which is to be limited only by the appended claims.

We claim:

1. A fluid recovery and transfer system comprising:
a plurality of rigid containers;
a collapsible container within each of said plurality of rigid containers, each of said collapsible containers respectively coupled to a common intake and a common output for a first fluid; and
a closed pumping circuit coupling said plurality of rigid containers;
pump means for pumping a second fluid contained in said closed pumping circuit to and from each of said plurality of rigid containers so as to hydraulically effect the alternate intake and output of said first fluid from each of said plurality of collapsible containers.

2. The fluid recovery and transfer system according to claim 1 wherein said plurality of rigid containers comprises two rigid containers.

3. The fluid recovery and transfer system according to claim 2 wherein said pump means comprises a unidirectional pump.

4. The fluid recovery and transfer system according to claim 1 wherein at least one of said plurality of collapsible containers is made of a semi-permeable dialysis material.

5. The fluid recovery and transfer system according to claim 4 wherein said at least one semi-permeable collapsible container includes a plurality of pleats.

6. The fluid recovery and transfer system according to claim 1 wherein a substance is bound to the interior of at least one of said plurality of collapsible containers for effecting treatment on the first fluid taken therein.

7. The fluid recovery and transfer system according to claim 1 further comprising:
   means for selectively charging said closed pumping circuit with said second fluid.

8. A body fluid recovery and transfer system comprising:
   a first and a second rigid container;
   a first and a second collapsible container respectively disposed within said first and said second rigid containers, said first and said second collapsible containers respectively coupled to a common intake and a common output for a body fluid; and
   pump means for pumping a pump fluid between said first and second rigid containers so as to hydraulically effect the alternate intake and output of said body fluid from said first and second collapsible containers.

9. The fluid recovery and transfer system according to claim 8 wherein at least one of said collapsible containers is semi-permeable.

10. The fluid recovery and transfer system according to claim 9 wherein said at least one same-permeable collapsible container includes a plurality of pleats.

11. The fluid recovery and transfer system according to claim 8 wherein a substance is bound to the interior of at least one of said plurality collapsible containers for effecting treatment on the body fluid taken therein.

12. In a medical fluid recovery and transfer system including first and second rigid containers, and first and second collapsible containers respectively disposed within said first and said second rigid containers, said first and said second collapsible containers respectively coupled to a common intake and a common output for a body fluid, a method of effecting the intake and output of said body fluid from said first and second collapsible containers comprising the alternative steps of:
   (a) pumping a pump fluid from said first rigid container to said second rigid container to hydraulically effect the output of said body fluid from said second collapsible container while simultaneously effecting the intake of said body fluid to said first collapsible container; and
   (b) pumping said pump fluid from said second rigid container to said first rigid container to hydraulically effect the output of said body fluid from said first collapsible container while simultaneously effecting the intake of said body fluid to said second collapsible container.

13. The method according to claim 12 wherein in step (s) the pumping of said pump fluid continues until said second collapsible container is empty and said first collapsible container is full; and in step (b) the pumping of said pump fluid continues until said first collapsible container is empty and said second collapsible container is full.

14. The method according to claim 12 wherein said pump fluid is a body compatible fluid.

15. The method of claim 14 wherein said first and second collapsible containers are made of a semi-permeable dialysis material.

16. The method according to claim 15 wherein said body compatible fluid is a dialysate for said body fluid.

17. In a medical fluid recovery and transfer system including first and second rigid containers, first and second semi-permeable collapsible containers respectively disposed within said first and second right containers, said first and said second semi-permeable collapsible containers respectively coupled to a common intake and a common output for a body fluid, a method of dialysis for said body fluid comprising the alternate steps of:
   (a) pumping a dialysate fluid from said first rigid container to said second rigid container so as to hydraulically effect the output of said body fluid from said second semi-permeable collapsible container while simultaneously effecting the intake of said body fluid to said first semi-permeable collapsible container; and
   (b) pumping said dialysate fluid from said second rigid container to said first rigid container so as to hydraulically effect the output of said body fluid from said first semi-permeable collapsible container while simultaneously effecting the intake of said body fluid to said second semi-permeable collapsible container;
   (c) said dialysate fluid having a suitable composition to establish a concentration gradient for a material to be dialyzed between said body fluid and said dialysate fluid to cause the transfer of said material through said semi-permeable container between said body fluid and said dialysate fluid.

18. The method according to claim 17 wherein said first and second semi-permeable collapsible containers include a plurality of pleats.

19. A pumping circuit for use with a medical fluid recovery and transfer system including first and second rigid containers and first and second collapsible containers respectively disposed within said first and second rigid containers, said first and second collapsible containers respectively coupled to a common intake and a common output for a body fluid, said pumping circuit comprising:
   tubing for establishing fluid communication between said first and second rigid containers; and
   pump means for pumping a pump fluid between said first and second rigid containers through said tubing so as to hydraulically effect the alternate intake and output of said body fluid from said first and second collapsible containers.

20. The pumping circuit according to claim 19 wherein said tubing is heprin impregnated polyethylene tubing.

21. The pumping circuit according to claim 19 wherein said pump means is a positive displacement pump.

22. The pumping circuit according to claim 19 further comprising:
   check valve means positioned in said tubing and responsive to pressure changes during operation of said pump means to control fluid flow in said tubing.

23. The pumping circuit according to claim 19 further comprising:
   valve means associated with said pump means to effect pulsatile flow by controlling the output of said pump means.

* * * * *